United States Patent
Listemann et al.

Patent Number: 5,180,851
Date of Patent: Jan. 19, 1993

[54] PREPARATION OF N-(L-ALKOXYALKYL)FORMAMIDE AND ALKYLIDENE BISFORMAMIDES USING AMINE NEUTRALIZED ION EXCHANGE RESINS

[75] Inventors: Mark L. Listemann, Whitehall; Robert K. Pinschmidt, Jr., Allentown, both of Pa.

[73] Assignee: Air Products and Chemicals Inc., Allentown, Pa.

[21] Appl. No.: 672,812

[22] Filed: Mar. 21, 1991

[51] Int. Cl.$^5$ .................................... C07C 231/02
[52] U.S. Cl. .................................... 564/134; 564/133; 564/139; 564/201; 564/205; 564/215
[58] Field of Search ............... 564/201, 134, 133, 187, 564/205, 215, 139

[56] References Cited

U.S. PATENT DOCUMENTS

| | | | |
|---|---|---|---|
| 4,334,097 | 6/1982 | Schmidth | 564/201 |
| 4,554,377 | 11/1919 | Stackman et al. | 564/205 |
| 4,567,300 | 1/1986 | Murae et al. | 564/215 |
| 4,942,259 | 7/1990 | Parris | 564/187 |

FOREIGN PATENT DOCUMENTS

| | | |
|---|---|---|
| 0332083 | 9/1989 | European Pat. Off. |
| 1125940 | 9/1968 | United Kingdom ............... 564/215 |
| 2152929 | 8/1985 | United Kingdom . |

OTHER PUBLICATIONS

Stackman, R. W.; Summerville, R. H., "Synthesis of N-Vinylacetamide and Preparation of Some Polymers and Copolymers" Ind. Eng. Chem. Prod. Res. Dev. 1985 24, 242-246.

*Primary Examiner*—Richard L. Raymond
*Assistant Examiner*—Shailendra Kumar
*Attorney, Agent, or Firm*—Russell L. Brewer; James C. Simmons; William F. Marsh

[57] ABSTRACT

This invention relates to an improved process for the formation of N-(l-alkoxyalkyl)amides with coproduction of alkylidene bisamides. The N-(l-alkoxyalkyl)formamides of this invention are prepared by reacting formamide with an acetal or hemiacetal carboxylate ester represented by the formulas below in the presence of a solid acid ion exchange resin wherein the acid groups have been neutralized with an amine compound having a pKa (as the protonated amine in water) from about 4 to 9. The hemiacetal ester is represented by formula I and the acetal is represented by formula II.

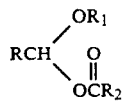

I

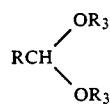

II

In the above formulas, R is $C_1$–$C_8$ alkyl, aralkyl or aryl; $R_1$ and $R_2$ are $C_1$–$C_8$ alkyl, or aryl; and $R_3$ is secondary or tertiary alkyl having from 3-8 carbon atoms.

16 Claims, No Drawings

PREPARATION OF N-(L-ALKOXYALKYL)FORMAMIDE AND ALKYLIDENE BISFORMAMIDES USING AMINE NEUTRALIZED ION EXCHANGE RESINS

TECHNICAL FIELD

This invention relates to an improved process for the preparation of N-(1-alkoxyalkyl)formamides and alkylidene bisformamides which are precursors to N-alkenyl formamides which can be polymerized to form water-soluble homopolymers and copolymers.

BACKGROUND OF THE INVENTION

N-vinylamides have long been used as monomers for the production of homopolymers and copolymers having valuable properties. The polymer resulting from the polymerization of N-vinylamide contains reactive hydrogens which can be used as sites for effecting cross-linking attachment of activated substrates onto the polymer or the amide may be hydrolyzed to form polyvinylamine which is suitable for other uses.

Parris, et al. in U.S. Pat. No. 4,942,259 disclose catalytic processes for the cracking of N-(alkoxyalkyl)formamides and N-(alkoxyalkyl)amides as well as the corresponding bis-amides to produce the corresponding N-alkenyl amides. The N-alkenyl amides then can be polymerized. Of these, it is the N-(1-alkoxyethyl)formamides and bisformamides that lend themselves to the Parris, et al. catalytic cracking process to form N-vinylformamide.

A number of routes for producing N-vinylcarboxylic amides have been suggested and these routes generally involve the production of either N-(alpha-alkoxyethyl)amides, alternatively referred to as N-(1-alkoxyethyl)-carboxylic acid amides. Representative patents and articles which illustrate preparation of N-vinylamides are as follows: Stackman in U.S. Pat. No. 4,554,377 and in an article entitled *Synthesis of N-vinylacetamide and Preparation of Some Polymers and Copolymers*, 24 Ind. Eng. Chem. Prod. Res. Dev., 242-246 (1985), disclose the reaction of acetamide with dimethyl acetal to form the N-(alpha-alkoxyethyl)carboxylic acid amide. In this reaction there is a competing equilibrium reaction and this reaction involves the subsequent reaction of the N-(alpha-alkoxyethyl)-carboxamide with another mole of alkylamide to form ethylidenebis(alkylamide), an unwanted co-product. The reaction is carried out in the presence of an acid, such as methanesulfonic acid or sulfuric acid. When formamide was substituted for acetamide, the reaction was unsuccessful (p. 244).

Schmidt, in U.S. Pat. No. 4,334,097, discloses a process for producing N-(alpha-alkoxyalkyl)carboxamides by reacting primary and secondary carboxamides with an alpha-halogen alkyl ether. Tertiary amines are added to the reaction system to react with hydrogen halide as it is formed. The tertiary amine hydrogen halide then can be filtered from the reaction product and removed.

Bestian in German Patent 1,273,533 discloses a process for producing N-(alpha-alkoxyalkyl)carboxylic acid amides by reacting a secondary amide with an acetal or hemiacetal. Representative acetals include those formed by the reaction of an aldehyde with primary and secondary alcohols, e.g., methanol, ethanol, isopropanol, and isobutanol. Acid catalysts including inorganic acids, such as hydrochloric acid; acid chlorides, such as sulfuryl chloride; and aromatic sulfonic acids and acid chlorides, such as p-toluenesulfonic acid and chloride thereof are suggested as being suited for effecting reaction between the secondary carboxylic acid amide and acetal or hemiacetal.

N-(1-alkoxyethyl)carboxylic acid amides have been prepared by the electrochemical alkoxylation of N-ethylcarboxylic acid amides and by the reaction of formamide with aldehydes. In this regard Murao, et al. disclose in U.S. Pat. No. 4,567,300 and equivalent GB 2 152 929, a process wherein acetaldehyde reacts with formamide in the presence of a weakly basic catalyst to yield solid N-(1-hydroxyethyl)formamide which, following catalyst neutralization, reacts with alcohols in the presence of an acid catalyst to yield N-(1-alkoxyethyl)formamide. This process is unattractive in that it requires two discrete steps, the handling of a solid intermediate and the disposal of salts.

European Patent Publication 0 332,083 discloses the preparation of N-(1-alkoxyalkyl)carboxylic acid amides by reacting formamide with acetals derived from primary alcohols to produce the N-(1-alkoxyalkyl)formamides along with the alkylidene bisformamide. This reaction, in contrast to the statements made by Stackman, et al., is successful but requires the utilization of large amounts of acid in order to force the reaction of formamide with the acetal of a primary alcohol to form the N-(1-alkoxyalkyl)formamide.

SUMMARY OF THE INVENTION

This invention relates to an improved process for the preparation of N-(1-alkoxyalkyl)formamides involving the reaction of formamide with an acetal or hemiacetal ester in the presence of an acid catalyst. The improvement resides in the utilization of an acetal derived by the reaction of an aldehyde with a secondary or tertiary alkanol or alkoxy alkanol or hemiacetal carboxylate ester and the utilization of an acid salt; preferably of a solid macroreticular ion exchange resin having acid functionality, such acid functionality having been neutralized with an amine having a pKa (as the protonated amine in water) of from about 4 to 9. The hemiacetal carboxylate is represented by Formula I; the acetal is represented by Formula II.

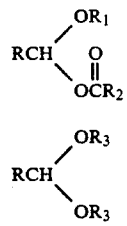

wherein R is $C_1$–$C_8$ alkyl, aralkyl or aryl; $R_1$ and $R_2$ are independently $C_1$–$C_8$ alkyl, or aryl; and $R_3$ is secondary or tertiary alkyl having from 3-8 carbon atoms.

Numerous advantages are achieved through the process of this invention, which include:

the ability to obtain high conversions of formamide to N-(1-alkoxyalkyl)formamide at lower catalyst levels than reported heretofore;

the ability to obtain N-(1-alkoxyalkyl)formamides and ethylidene bisformamide in high selectivity; and, the ability to minimize consumption of acid catalyst in achieving excellent conversion of formamide to N-(1-alkoxyalkyl)formamide and ethylidenebisformamide through increased catalyst selectivity ratios.

DETAILED DESCRIPTION OF THE INVENTION

The preparation of N-(1-alkoxyalkyl)formamide is accomplished by the reaction of acetals and hemiacetal carboxylate esters described by the formulas recited above with formamide. The general process is more particularly shown in copending application having U.S. Ser. No. 07/631597 and a filling date of Dec. 21, 1990. The subject matter of that application is incorporated by reference.

One type of acetal suited for the process described herein is formed by reacting an alkylaldehyde with a secondary or tertiary alcohol, or with an alkoxyalkanol having a secondary or tertiary alcohol group. Another is a hemiacetal ester formed by reacting an alkylaldehyde with an alcohol and alkylcarboxylic acid. Representative acetals and hemiacetal carboxylate esters include acetaldehyde diisopropyl acetal; acetaldehyde diisobutyl acetal; acetaldehyde ethyl isopropyl acetal; acetaldehyde isopropyl isobutyl acetal; isobutyraldehyde diisobutyl acetal; isobutyraldehyde diisopropyl acetal. Hemiacetal carboxylate esters include acetaldehyde ethyl hemiacetal acetate ester, acetaldehyde isopropyl hemiacetal acetate ester; acetaldehyde isobutyl hemiacetal acetate ester; acetaldehyde t-butyl hemiacetal acetate ester and the like. When considering the acetals, it is preferred that both of the acetal groups are from a secondary or tertiary alcohol, and are identical. In contrast, the hemiacetal carboxylate ester may incorporate primary organic groups where $R_1$ and $R_2$, are methyl and ethyl or $R_1$ and $R_2$ may be secondary or tertiary groups. In a preferred case $R_1$ is isopropyl or t-butyl and $R_2$ is methyl. However, in both the acetal and hemiacetal carboxylate ester, it is preferred that R is methyl.

The reaction of formamide with mixed acetals derived from a primary alcohol and a secondary or tertiary alcohol tends to be slightly worse than where both of the acetal groups are derived from secondary or tertiary alcohols. The use of an acetal having ether groups derived from a mixture of both primary and secondary alcohols also tends to create problems in separation and reduces conversion. In that regard they can have a negative effect upon the overall reaction performance.

Catalysts suited for effecting reaction between formamide and the acetal are amine salts of strong acids. Preferred catalysts are solid, especially macroreticular strong acid ion exchange resins which have been neutralized with an amine. Examples of ion exchange resins which can be converted to suitable catalysts for this reaction include strene-divinylbenzene crosslinked resins, phenol-aldehyde, and polyfluorinated resins functionalized with sulfonic acid groups. Representative fluorinated polymer networks containing sulfonic acid groups are sold under the trademark Nafion. Representative styrene-divinylbenzene crosslinked ion exchange resins containing sulfonic acid groups are sold under the trademark Amberlyst.

The acidic catalysts are neutralized with a relatively weak base, e.g., an amine having a basicity expressed in pKa units (as the protonated amine in water) from 4 to 9. Amines having the desired basicity include weakly basic tertiary amines such as pyridine, substituted pyridines, anilines, quinolines, and toluidines. Amines having pKa values from about 5 to 6 are especially preferred. Alkyl amines generally are too basic; the resulting amine acid salts have too little acidity and catalyst activity is reduced. When the pKa is too low, there may be enhanced reactivity but with concomitant reduction in selectivity and the catalyst selectivity ratio may decrease.

Temperatures suited for effecting reaction between formamide and the acetals range from about 60° to 200° C. with preferred temperatures ranging from 80°–130° C. Pressures required for the reaction range from subatmospheric to autogenous. Under the reaction conditions generally specified, reaction times will range from about 1–24 hours with the reaction typically taking from about 2–4 hours.

The mole ratio of formamide to acetal derived from a secondary or tertiary alcohol, etc., may range from 0.2 to 6 moles, and preferably 1.5 to 3 moles of formamide per one (1) mole of acetal or hemiacetal ester. When the mole ratio of formamide to acetal is increased above about 4:1, no significant advantages are seen and when the ratio falls below about 1:1, the selectivity with respect to acetal may suffer. In contrast to the prior art processes, the reaction of an acetal of a secondary or tertiary alcohol with formamide leads to the formation of high yields of N-(1-alkoxyalkyl)formamide and alkylidene bisformamide at lower mole ratios of acetal to amide. Furthermore, the use of catalysts which are solid phase ion exchange resins wherein the acid groups have been neutralized with a relatively weak base increases the catalyst selectivity ratio. Simultaneous distillation of coproduct alcohol from the reaction mixture may be used to improve the overall conversion and increase the ratio of Bis to alkoxyalkylformamide.

The catalyst is incorporated in the reaction within a range from about 0.01 to 0.1 (preferably 0.03–0.1) moles per moles acetal charged to the system. Although concentrations as high as 0.2 moles catalyst per mole acetal can be utilized, the excess catalyst seems to afford no significant advantages and in fact is deactivated much more quicky than at lower levels.

The reaction may be carried out neat or in a solvent and representative solvents include secondary and tertiary alkanols having from 1 to 8 carbon atoms, e.g., isopropanol, isobutanol, tert-butanol and so forth; acetonitrile, and high boiling ethers such as diisobutyl ether, dimethylglycol ether, tetraglyme, tetrahydrofuran and dioxane. There are essentially three criteria for the solvent, one is that it is capable of forming a single acetal/amide/solvent liquid phase; two it is not a good nucleophile with a reactive hydrogen; and, three the solvent is inert in the reaction medium.

The following examples are provided to illustrate various embodiments and are not intended to restrict the scope thereof.

EXAMPLE 1

Preparation of N-(1-Isopropoxyethyl)formamide, and Comparative Acetals and Non-Neutralized Catalyst Systems N-(1-Isopropoxyethyl)formamide and related compositions were prepared in the conventional manner by reacting formamide with the appropriate acetal. More particularly, the reactants added to provide preselected mole equivalents of acetal (m) per mole of formamide (n) were charged to a stirred flask at which time a solid phase macroreticular ion exchange resin with sulfonic acid groups (Amberlyst 15) was also added. At the completion of the reaction, the resin was filtered therefrom. The product was collected and analyzed.

Table 1 below sets forth the reaction conditions and analysis of products including conversion based upon formamide charged.

lyst selectivity ratios drop as the amount of formamide is increased, but remain appreciably higher than those obtained using the ethyl acetal. Run 10 shows that replacing the isopropanol with a non-reactive solvent (acetonitrile) further decreases catalyst deactivation without lowering selectivity or conversion.

The catalyst selectivity ratio is the ratio of product yields (REF+Bis) to alkyl formate yield. The amount of alkyl formate is a measure of catalyst deactivation. The higher the catalyst selectivity ratio, the more product is produced relative to the amount of catalyst which becomes inactive.

TABLE 1

Comparison of Ethyl and Isopropyl Acetaldehyde Acetals $$m\ CH_3CH(OR)_2 + n\ H_2NCHO + x\ ROH \longrightarrow CH_3CH(OR)NHCHO\ \text{and}\ CH_3CH(NHCHO)_2$$

| Run | Mole %[a] Catalyst | R | Acetal (m) | Formamide (n) | Alcohol (x) | Temp (°C.) | Time (hrs) | % Yields[a] REF[f] | Bis[g] | HCOOR[h] | Acetal[b] Conv (%) | Formamide[b] Conv (%) | Selectivity[c] (Acetal) | Selectivity[d] (Formamide) | Catalyst Selectivity[e] Ratio |
|---|---|---|---|---|---|---|---|---|---|---|---|---|---|---|---|
| 1 | 18 | Et | 2 | 1 | 0 | 80 | 2 | 59 | 7 | ~16 | 40 | 91 | 83 | 81 | 4 |
| 2 | 18 | Et | 2 | 1 | 0 | 60 | 3 | 68 | 5 | ~16 | 51 | 94 | 71 | 82 | 5 |
| 3 | 18 | Et | 1 | 1 | 0 | 25 | 4 | 45 | 3 | 9 | 61 | 74 | 79 | 70 | 5 |
| 4 | 10 | Et | 1 | 1.5 | 1 | 40 | 3 | 33 | 2 | 12 | 39 | 27 | 91 | 95 | 3 |
| 5 | 5 | i-Pr | 1 | 1 | 1 | 40 | 3 | 49 | 14 | 1.6 | 68 | 74 | 93 | 98 | 39 |
| 6 | 10 | i-Pr | 1 | 1 | 1 | 40 | 3 | 54 | 17 | 1.9 | 80 | 95 | 88 | 92 | 37 |
| 7 | 10 | i-Pr | 1 | 1.2 | 1 | 40 | 3 | 62 | 21 | 3.2 | 90 | 92 | 93 | 95 | 26 |
| 8 | 10 | i-Pr | 1 | 1.5 | 1 | 40 | 3 | 59 | 34 | 3.2 | 95 | 87 | 98 | 98 | 29 |
| 9 | 10 | i-Pr | 1 | 2.0 | 1 | 40 | 3 | 55 | 39 | 4.2 | 96 | 72 | 98 | 93 | 22 |
| 10 | 10 | i-Pr | 1 | 1.5 | 1[i] | 40 | 3 | 56 | 41 | 2 | 93 | 89 | 100 | 98 | 48 |

[a]Mole % catalyst and % yields vs. the limiting reagent.
[b]Conversions expressed as a percentage of the initial reactant amount.
[c]Selectivity vs. acetal = [% yields (REF + Bis)/(Acetal conv. × m)] × 100.
[d]Selectivity vs. Formamide = [% yields (REF + 2 × Bis)/(formamide conv. × n)] × 100
[e]Catalyst selectivity ratio = % yields (REF + Bis)/(% yield of HCOOR)
[f]REF = N-(1-alkoxyethyl)formamide, $CH_3CH(OR)NHCHO$.
[g]Bis = Ethylidene bisformamide, $CH_3CH(NHCHO)_2$.
[h]HCOOR is the alkyl formate derived from catalyst deactivation according to: $H^+ + H_2NCHO + ROH \rightarrow HCOOR + NH_4^+$.
[i]In this run 1 equivalent of acetonitrile was used rather than isopropanol.

Runs 1 and 2 demonstrate that high catalyst loadings (18 mole %) and an excess of the primary acetal, i.e., acetaldehyde ethyl acetal (2:1 acetal to formamide ratio) are required to obtain high formamide conversions with good selectivities. In this type of reaction large amounts of acid catalyst are required. Note that the catalyst is almost completely deactivated during the run by stoichiometric reaction with formamide and alcohol to give formate (refer to the low catalyst selectivity ratio) and, therefore, the catalyst must be regenerated prior to reuse. Run 4 shows that addition of ethanol and lowering the acetal to amide ratio improves selectivity but further lowers conversion, because ethanol also causes rapid catalyst deactivation.

Runs 5-10 show the results obtained from the substitution of a hindered acetal derived from the secondary alcohol, isopropanol, for the primary acetal, acetaldehyde ethyl acetal. Runs 6-10 show that by increasing the formamide to acetal ratio from 1 to 2, one can increase acetal conversion from 80 to 95% while formamide conversion decreases from 95 to 72%. The cata-

EXAMPLE 2

Effect of Amine on Catalyst Activity and Selectivity

The procedure of Example 1 was repeated except that the desired mole ratios of amide, acetal and solvent were charged to a three neck flask equipped with a reflux condenser, inert gas inlet, mechanical stirrer and stopper. The acid ion exchange catalyst was rapidly charged to the stirred liquids and the flask heated to the desired temperature. Aliquots were removed by syringe and analyzed by gas chromotography using a Quadrex OV-1701 25 m×0.53 mm i.d. capillary column with a 3μ film thickness. Table 2 sets forth the results.

TABLE 2

Effect of Amine and Acetal on Activity and Selectivity

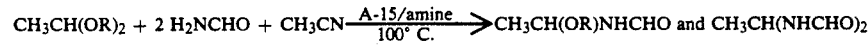

$$CH_3CH(OR)_2 + 2\ H_2NCHO + CH_3CN \xrightarrow[100^\circ C.]{A-15/\text{amine}} CH_3CH(OR)NHCHO\ \text{and}\ CH_3CH(NHCHO)_2$$

| Run # | R | Amine[a] (eq.) | Time (hr) | % Yields[a] REF[f] | Bis[g] | HCOOR[h] | Acetal[b] Conv. | Formamide[b] Conv. | Acetal[c] Sel. | Formamide[d] Sel. | Catalyst Selectivity[e] Ratio |
|---|---|---|---|---|---|---|---|---|---|---|---|
| 1 | i-Pr | NEt3 (0.10) | 1 | 4.2 | 1.3 | <0.2 | 6.9 | 14.1 | 79.8 | 23.9 | — |
|   |      |              | 2 | 9.1 | 4.6 | <0.2 | 17.1 | 14.6 | 80.1 | 62.8 | — |
|   |      |              | (120° C.) | | | | | | | | |
| 2 | i-Pr | NH3 (0.092) | 1 | 15.5 | 5.4 | <0.2 | 35.2 | 16.4 | 59.3 | 80.2 | 60.5 |
|   |      |              | 3 | 18.1 | 10.3 | 0.5 | 46.8 | 22.1 | 60.7 | 87.5 | 40.8 |
|   |      |              | 5 | 18.8 | 12.2 | 0.8 | 51.8 | 24.8 | 59.8 | 87.2 | 32.6 |
| 3 | i-Pr | pyridine (0.073) | 1 | 23.8 | 38.4 | 0.5 | 59.9 | 51.5 | 100 | 97.7 | 119.7 |
|   |      |              | 2 | 24.2 | 47.8 | 0.9 | 72.8 | 63.8 | 98.9 | 93.9 | 82.8 |

TABLE 2-continued

Effect of Amine and Acetal on Activity and Selectivity $$CH_3CH(OR)_2 + 2\ H_2NCHO + CH_3CN \xrightarrow[100°\ C.]{A-15/amine} CH_3CH(OR)NHCHO\ \text{and}\ CH_3CH(NHCHO)_2$$

| Run # | R | Amine[a] (eq.) | Time (hr) | % Yields[a] REF[f] | Bis[g] | HCOOR[h] | Acetal[b] Conv. | Formamide[b] Conv. | Acetal[c] Sel. | Formamide[d] Sel. | Catalyst Selectivity[e] Ratio |
|---|---|---|---|---|---|---|---|---|---|---|---|
|   |   |   | 3 | 24.9 | 54.8 | 1.2 | 77.8 | 68.2 | 100 | 98.7 | 65.9 |
| 4 | Et | pyridine (0.073) | 1 | 20.7 | 10.5 | 1.1 | 37.4 | 56.9 | 83.4 | 73.3 | 28.4 |
|   |   |   | 2 | 24.5 | 13.9 | 1.9 | 44.9 | 69.7 | 85.5 | 75.0 | 20.2 |
|   |   |   | 3 | 27.3 | 17.0 | 2.3 | 53.2 | 76.5 | 83.3 | 80.1 | 19.3 |

[a]Equivalents of catalyst and % yields relative to the acetal.
[b]Conversions expressed as a percentage of the inital reactant amount.
[c]Selectivity with respect to the acetal = [% yields (REF + Bis)/(Acetal conv.)] × 100
[d]Selectivity with respect to formamide = [% yields (REF + 2 × Bis)/(formamide conv. × 2)] × 100
[e]Catalyst Selectivity ratio = % yields (REF + Bis)/(% yield HCOOR).
[f]REF = N-(1-alkoxyethyl)formamide, $CH_3CH(OR)NHCHO$.
[g]Bis = ethylidene bisformamide, $CH_3CH(NHCHO)_2$.
[h]HCOOR is the alkyl formate derived from catalyst deactivation according to: $H^+ + H_2NCHO + ROH \rightarrow HCOOR + NH_4^+$.

Run 1 demonstrates that neutralizing the A-15 sulfonic acid catalyst with a highly basic amine such as triethylamine (pKa=11.0) results in low reactant conversions and moderate selectivities. Moving to ammonia (pKa=9.2), which is less basic but contains active protons (Run 2), raises the conversions but lowers selectivity with respect to the acetal. In contrast, pyridine (Run 3) (pKa=5.2) affords good conversions and excellent selectivities with respect to both reactants. Note that the pKa's refer to the protonated amine in water. The larger the pKa, the more basic the amine. The less reactive ethyl acetal (run 4) affords lower acetal conversion and lower selectivities with respect to both reactants than does the isopropyl acetal. However, even with the ethyl acetal the catalyst selectivity ratio is significantly improved over those obtained from the non-poisoned acid catalysts.

Additionally catalyst life is extended through the use of an acid catalyst neutralized with an amine having a pKa about 4 to 9 (as the acid salt in water) than it is as the non-neutralized acid. This is reflected in the catalyst selectivity ratio.

The catalyst selectivity ratio is the ratio of product yields (REF+Bis) to alkyl formate yield. The amount of alkyl formate is a measure of catalyst deactivation. The higher the catalyst selectivity ratio, the more product is produced relative to the amount of catalyst which becomes inactive. The combination of A-15/pyridine with the highly reactive isopropyl acetal (run 3) is clearly superior to the ethyl acetal (run 4) under otherwise identical conditions.

COMMENTARY

In an effort to explain the benefits obtained from using an acetal derived from a secondary or tertiary alcohol or a hemiacetal carboxylate ester and an amine neutralized acid catalyst as described in Examples 1 and 2, the following is provided. Acetaldehyde diisopropyl acetal, $CH_3CH(O-i-Pr)_2$, an acetal derived in part by reacting acetaldehyde with the secondary alcohol, isopropanol, is sterically hindered, and thus loses isopropanol more readily than an unhindered primary acetal such as acetaldehyde diethyl acetal would lose ethanol. The steric hindrance provides a driving force for reaction which is seen experimentally in the lower catalyst loadings and temperatures required for the reaction with acetaldehyde diisopropyl acetal versus acetaldehyde diethyl acetal.

In a serious competing reaction, amides also react stoichiometrically with acids in the presence of water or alcohols as shown below (equation 1). The reaction of an amide with water forms the corresponding carboxylic acid and an amine salt of the strong acid catalyst $H^+X^-$. Neither the carboxylic acid nor the amine salt are sufficiently acidic to efficiently catalyze the desired reaction. Similarly, reaction of an amide and an acid in alcohol forms an ester and the amine salt of the acid catalyst (equation 2). If these reactions take place to a significant extent, the acid catalyst needed for the N-(1-alkoxyalkyl)amide and alkylidene bisformamide synthesis is consumed and the selectivity is lowered due to consumption of the amide reactant.

$$R_1CONHR_2 + H_2O + H^+X^- \rightarrow R_1COOH + R_2NH_3^+X^- \qquad 1.$$

$$R_1CONHR_2 + R_3OH + H^+X^- \rightarrow R_1COOR_3 + R_2NH_3^+X^- \qquad 2.$$

The reactions set forth above aid in explaining the changes associated with the use of formamide and, to a lesser extent, other amides as a reactant with an acetal of a primary versus an acetal of a secondary alcohol as well as with a hemiacetal carboxylate acid ester in the presence of an acid catalyst versus with an amine neutralized acid ion exchange catalyst. For example, reaction 1 above proceeds at a faster rate than does reaction 2. However, both reactions 1 and 2 proceed at a faster rate when $R_1$ is hydrogen (as in formamide) than when $R_1$ is alkyl (as in acetamide). When $R_1$ is hydrogen, both reactions proceed at a rate such that the acid catalyst and formamide are consumed before complete reaction of formamide with the acetal can take place. As a result, selectivity to N-(1-alkoxyalkyl)formamide and bisformamide, based on formamide charged, is poor when water is present or the alcohol is highly reactive with the amide.

The runs in Example 1 also illustrate an additional advantage which is explained by reaction 2. Secondary and tertiary alcohols derived from acetals of secondary or tertiary alcohols, when released during the reaction between formamide and the acetal of a secondary or tertiary alcohol, will react more slowly with formamide and acid than will the corresponding primary alcohol when released. However, in either case, it is preferred that any alcohol is distilled away as it is formed in order to enhance catalyst life and selectivity. This also causes the reaction to proceed toward bisformamide formation. Lastly, the neutralization of the acid ion exchange catalyst with a weakly basic amine reduces its reactivity with alcohol and formamide but leaves sufficient acidity to catalyze the reaction of formamide with the acetal or hemiacetal carboxylate ester.

To summarize:

Sterically hindered acetals and hemiacetal esters have higher reactivity with formamide, which allows lower catalyst loadings and reaction temperatures, and minimizes recycle; and two Sterically hindered secondary and tertiary alcohols or carboxylic acids deactivate the acid catalyst much more slowly in the presence of formamide than primary alcohols or water.

Catalyst deactivation is further minimized by lowering the acidity of the acid catalyst by the addition of certain amines. The amine-poisoned catalyst retains sufficient activity to catalyze the reaction of formamide with a reactive, sterically hindered acetal, but is less prone to deactivation. Catalyst deactivation requires protonation of formamide followed by nucleophilic attack by an alcohol or water. This reaction is more sensitive to the strength of the acid catalyst than is the hindered acetal-formamide reaction.

EXAMPLE 3

Distillation during the reaction of Example 2 was conducted in the following manner. Table 3 sets forth the conditions and results after distillation.

TABLE 3

Effect of Distillation on Product Distribution $$CH_3CH(O\text{-}i\text{-}Pr)_2 + 2\,H_2NCHO + CH_3CN \xrightarrow[\text{distill}]{\text{A-15/amine}} CH_3CH(OR)NHCHO \text{ and } CH_3CH(NHCHO)_2$$

| Run # | Amine[a] (eq.) | Time (hr) | Temp (°C.) | % Yields[a] i-PrEF | Bis | Acetal[b] Conv. | Formamide[b] Conv. | Acetal[c] Sel. | Formamide[d] Sel. |
|---|---|---|---|---|---|---|---|---|---|
| 1 | $NH_3$ (0.092) | 1 | 120 | 18.4 | 13.7 | 53.7 | 35.2 | 59.8 | 65.1 |
| 2 | pyridine (0.073) | 1 | 120 | 3.3 | 62.6 | 71.7 | 72.3 | 91.9 | 88.9 |
| 3 | pyridine (0.073) | 1.5 | 100 | | | | | | |
| | | 1 | 120 | 6.8 | 68.5 | 82.9 | 80.8 | 90.8 | 88.9 |

[a]Mole % catalyst and % yields vs. the limiting reagent.
[b]Conversions expressed as a percentage of the initial reactant amount.
[c]Selectivity vs. acetal = [% yields (REF + Bis)/(Acetal conv. × m)] × 100.
[d]Selectivity vs. Formamide = [% yields (REF + 2 × Bis)/(formamide conv. × n)] × 100

In Example 3 volatile products are distilled out during the course of the reactions. Run 1 shows that ammonia neutralized A-15 still affords only moderate selectivities with respect to both reactants. Run 2 demonstrates that with the active A-15/pyridine catalyst the product distribution can be shifted to favor the Bis product as byproduct isopropanol is removed. Run 3 shows that heating the reaction at 100° C. for 1.5 hours before beginning distillation at 120° C. increases conversions by 10-12%. Thus the reaction is quite rapid with byproduct removal (compare to Example 1, Run 3) and excellent selectivities are maintained. In some applications, product distributions favoring Bis are preferred. Thus, distillation during the course of the reaction serves to increase the rate of the reaction and should lower catalyst deactivation by removing free alcohol which could otherwise react with formamide to cause catalyst deactivation.

What is claimed is:

1. In a process for the preparation of N-(1-alkoxyalkyl)amides and alkylidene bisamides wherein an alkylamide is reacted with an ether containing composition in the presence of an acid catalyst, the improvement for producing N-(1-alkoxyalkyl)formamides and alkylidene bisformamides which comprises:

(a) reacting formamide with an ether containing composition selected from the group consisting of an acetal or hemiacetal carboxylate ester represented by the formulas:

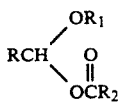

I

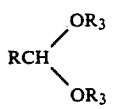

II wherein R is $C_1$-$C_8$ alkyl, hydrocarbyl aralkyl or hydrocarbyl aryl; $R_1$ and $R_2$ are independently $C_1$-$C_8$ alkyl, or hydrocarbyl aryl; and $R_3$ is secondary or tertiary alkyl having from 3-8 carbon atoms and (b) effecting said reaction of formamide with said acetal or hemiacetal carboxylate ester in the presence of a strong acid ion exchange resin neutralized with an amine having a basicity expressed as pKa of the protonated amine in water ranging from about 4 to 9.

2. The process of claim 1 wherein the ether containing composition is represented by Formula II, R is methyl, and the catalyst is neutralized with a weakly basic amine.

3. The process of claim 2 wherein the catalyst is present in an amount from 0.03 to 0.1 moles catalyst per mole of acetal.

4. The process of claim 3 wherein $R_2$ and $R_3$ are isopropyl.

5. The process of claim 3 wherein $R_2$ and $R_3$ are t-butyl.

6. The process of claim 3 wherein the amine used to neutralize the catalyst is selected from the group consisting of pyridine, and substituted pyridines, quinolines, toluidines and anilines.

7. The process of claim 3 wherein the mole ratio of formamide to acetal is from 0.5 to 4:1 and the pKa of the amine is from about 5-6.

8. The process of claim 7 wherein at least a portion of the alcohol generated during the reaction of formamide with the acetal is removed during the reaction.

9. The process of claim 1 wherein the ether-containing composition is represented by Formula I and R is methyl.

10. The process of claim 9 wherein the amine used to neutralize the catalyst is a weakly basic tertiary amine.

11. The process of claim 10 wherein the catalyst is present in an amount from 0.03 to 0.1 moles catalyst per mole of the hemiacetal carboxylate ester.

12. The process of claim 11 wherein the amine used to neutralize the catalyst is selected from the group consisting of pyridine, and substituted pyridines, toluidines, anilines and quinolines.

13. The process of claim 11 wherein the mole ratio of formamide to hemiacetal carboxylate ester is from 0.5 to 4:1 and the pKa of the amine is from about 5–6.

14. The process of claim 12 wherein at least a portion of the alcohol generated during the reaction of formamide with the hemiacetal carboxylate ester is removed during the reaction.

15. The process of claim 13 wherein $R_1$ is isopropyl and $R_2$ is methyl.

16. The process of claim 13 wherein $R_1$ is t-butyl and $R_2$ is methyl.

* * * * *